(12) United States Patent
Kishimoto et al.

(10) Patent No.: US 8,030,018 B2
(45) Date of Patent: Oct. 4, 2011

(54) METHOD FOR MEASURING ENZYMATIC ACTIVITY IN VIVO BY USE OF LASER

(75) Inventors: Tauya Kishimoto, Tokyo (JP);
Hidetoshi Watanabe, Chiba (JP);
Michihiro Ohnishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 237 days.

(21) Appl. No.: 12/110,969

(22) Filed: Apr. 28, 2008

(65) Prior Publication Data

US 2008/0299541 A1    Dec. 4, 2008

(30) Foreign Application Priority Data

May 28, 2007 (JP) ................................. 2007-139891

(51) Int. Cl.
*C12Q 1/26*        (2006.01)
(52) U.S. Cl. ........................................ 435/25; 424/9.1
(58) Field of Classification Search ................ 435/4, 25; 424/9.1
See application file for complete search history.

(56) References Cited

U.S. PATENT DOCUMENTS

| 2006/0270032 A1* | 11/2006 | Bhatia et al. | 435/325 |
| 2009/0018331 A1* | 1/2009 | Yoshikawa et al. | 544/95 |
| 2011/0014653 A1* | 1/2011 | Rapp | 435/69.6 |

FOREIGN PATENT DOCUMENTS

| EP | 0921396 A3 | 5/2000 |
| EP | 1243658 | 11/2008 |
| JP | 11-225791 | 8/1999 |
| JP | 2006-034215 | 2/2006 |

OTHER PUBLICATIONS

Dygert J. et al. Intracoronary Shunt Induced Endothelial Cell Damage in Porcine Heart. J of Surgical Research 131(2)168-174, Apr. 1, 2006.*
Mahmood U. et al. Near Infrared Optical Imaging of Protease Activity for Tumor Detection. Radiology 213(3)866-870, Dec. 1999.*
Piston D. Imaging Living Cells and Tissues by Two Photon Excitation Microscopy. Trends in Cell Biology vol. 9 Feb. 1999, 66-69.*
Squirrell J. et al. Long Term Two Photon Fluorescence Imaging of Mammalian Embryos Without Compromising Viability. Nature Biotechnology 17(8)763-7, Aug. 1999.*
Stresser et al., "Cytochrome P450 fluorometric substrates: Identification of isoform-selective probes for RAT CYP2D2 and human CYP3A4," American Society for Pharmacology and Experimental Therapeutics, vol. 30, pp. 845-851, 2002.
Lampe et al., "Time-Resolved Fluorescence Studies of Heterotropic Ligand Binding to Cytochrome P450 3A4," Biochemistry, vol. 45, pp. 12204-12215, 2006.
Dygert, James H., et al., "Intracoronary Shunt-Induced Endothelial Cell Damage in Porcine Heart," Journal of Surgical Research, vol. 131, pp. 168-174, 2006.
Heinze, Katrin G., et al., "Simultaneous two-photon excitation of distinct labels for dual-color fluorescence crosscorrelation analysis," PNAS, vol. 97, pp. 10377-10382, 2000.
Mahmood, Umar et al., "Near-Infrared Optical Imaging of Protease Activity for Tumor Detection," Radiology, vol. 213, pp. 866-870, 1999.
Zhong, Cheng F., et al., "Multiphoton in vivo Flow Cytometry," 2005 Conference on Lasers & Electro-Optics, pp. 2145-2147, 2005.

* cited by examiner

*Primary Examiner* — Ralph Gitomer
(74) *Attorney, Agent, or Firm* — K&L Gates LLP

(57) ABSTRACT

A method of measuring an enzymatic activity, includes measuring the quantity of a substrate metabolite produced upon metabolism of a substrate by an enzyme, through detecting a radiant wave generated from a multiple photon excitation process of the substrate or the substrate metabolite.

11 Claims, 4 Drawing Sheets

METHOD FOR MEASURING ENZYMATIC ACTIVITY IN VIVO BY USE OF LASER

CROSS REFERENCES TO RELATED APPLICATIONS

The present application claims priority to Japanese Patent Application JP 2007-139891 filed in the Japan Patent Office on May 28, 2007, the entire contents of which is being incorporated herein by reference.

BACKGROUND

The present disclosure relates to a method of measuring the activity of an enzyme, and the like. More particularly, the disclosure relates to a method of measuring the activity of an enzyme by use of a multiple photon excitation process, and the like.

Measurement of enzymatic activities in a tissue or cell has been conducted by biochemical techniques. First, a part of a tissue is taken out to prepare a homogenate, or cultured cells are harvested to prepare a lysate. Next, the tissue homogenate or cell lysate is centrifuged to prepare an enzymatically active fraction. Then, a reagent to be a substrate for an enzyme is added to the enzymatic active fraction thus prepared, and the quantity of a substrate metabolite produced upon a reaction between the substrate reagent and the enzyme is measured, to thereby measure the enzymatic activity.

In a colorimetric method, for example, a substrate reagent capable of coloring by reaction with the enzyme is used, and the degree of coloring is determined to thereby measure the enzymatic activity. Other examples of the measuring method include a fluorometric method in which a substrate reagent showing fluorescence by reacting with an enzyme is used and the intensity of fluorescence is determined to thereby measure the enzymatic activity, and an absorptiometric method in which a substrate having an absorption wavelength varied through reaction with an enzyme is used and the variation in absorbance is determined to thereby measure the enzymatic activity.

Japanese Patent Laid-open No. 2006-34215 describes a preparation method for cytochrome P450 (hereinafter referred to as "CYP450"), which is a representative drug-metabolizing enzyme. Besides, Analytical Biochemistry 276: 214-226, 1999 describes measurement of enzymatic activity by use of CYP450 obtained by this method or the like. In addition, American Society for Pharmacology and Experimental Therapeutics DMD 30:845-852, 2002 and Biochemistry 45:12204-12215, 2006 each disclose enzymatic activity measurement by use of CYP450 produced using a gene-recombined microorganism. Further, Japanese Patent Laid-open No. Hei 11-225791 describes enzymatic activity measurement in which a drug given to an animal is metabolized in vivo and the animal's urine is obtained to obtain CYP450.

In the methods of measuring an enzymatic activity according to the related art, the tissue homogenate or cell lysate and the enzymatically active fraction have to be prepared, which needs troublesome processes. Besides, in the methods of the related art, the tissue or cell has to be dissolved, so that it is very difficult to measure the activity, of an enzyme inside the tissue or cell while keeping the tissue or cell alive.

Thus, there is a need for a method of measuring an enzymatic activity in which measurement can be carried out by simpler operations, as compared with the methods according to the related art, and by which the activity of an enzyme present inside an in vivo tissue or an in vivo cell can also be measured.

SUMMARY

According to one embodiment, there is provided a method of measuring an enzymatic activity, including measuring the quantity of a substrate metabolite produced upon metabolism of a substrate by an enzyme, through detecting a radiant wave generated from a multiple photon excitation process of the substrate or the substrate metabolite.

Preferably, the measurement of enzymatic activity is carried out under such a condition that only one of the substrate and the substrate metabolite comes to generate the radiant wave through the multiple photon excitation process.

Especially, where the enzyme is an in vivo enzyme, the enzymatic activity measurement is preferably conducted by causing the substrate to penetrate into an in vivo site where the enzyme is present.

In addition, according to another embodiment, there are provided a method of measuring an enzymatic activity promoter or inhibitor, including measuring the quantity of a substrate metabolite produced upon metabolism of a substrate by an enzyme in the presence of the enzymatic activity promoter or inhibitor, through detecting a radiant wave generated from a multiple photon excitation process of the substrate or the substrate metabolite. There are further provided a method of screening an enzymatic activity promoter and/or inhibitor, including measuring the quantity of a substrate metabolite produced upon metabolism of a substrate by an enzyme in the presence of a specimen, through detecting a radiant wave generated from a multiple photon excitation process of the substrate or the substrate metabolite.

Furthermore, according to a further embodiment, there is provided an apparatus for measuring an enzymatic activity, including, at least: a laser beam source for generating a near infrared femtosecond laser beam for inducing a multiple photon excitation process of a substrate or substrate metabolite; a radiant wave detecting unit for detecting a radiant wave generated from the multiple photon excitation process of the substrate or substrate metabolite; and an optical path through which the near infrared femtosecond laser beam is introduced into a site where the enzyme is present and through which the radiant wave is introduced into the radiant wave detecting unit.

Besides, the apparatus may include a penetration device for introducing the substrate into the site where the enzyme is present.

The methods of measuring an enzymatic activity according to the embodiments are particularly suitable for application to the cases where the enzyme is a drug-metabolizing enzyme.

Definitions of terms used herein are given below.

The expression "multiple photon excitation process" means a phenomenon in which one molecule simultaneously absorbs a plurality of photons (multiple photon absorption), resulting in transition to or above the first excited stat of electron. The multiple photon excitation process can be induced by condensing a femtosecond laser beam, namely, a laser beam with a pulse width in the range of from femtosecond order to picosecond order (sub-picosecond range), onto a target molecule by an objective lens. The molecule thus excited generates a radiant wave when returning to its original energy state. By detecting the radiant wave, the molecule in the sample can be observed.

In the multiple photon excitation process, excitation is effected by the plurality of photons. Therefore, it is possible to use a longer-wavelength laser having a lower energy, as compared to the single photon excitation in the related art. Besides, the multiple photon excitation process occurs only when a plurality of photons reach the same molecule substantially simultaneously, and, therefore, the process is induced only in the vicinity of the focus of the laser. Further, since the long wavelength laser excellent in depth reaching performance is used, it is possible to excite the target molecules present in the range from the surface to the depth of the sample.

The term "radiant wave" herein means light generated when the molecule having made transition to an excited state returns to its original energy state. The "radiant wave" includes fluorescent light and, where the molecule is semiconductor, quantum dot, laser light, terahertz wave, etc. Incidentally, the term "reflected wave" herein is used in a meaning different from that of the "radiant wave": the "reflected wave" means the light which is not based on the multiple photon excitation process and which is simply reflected by the sample.

According to the method and apparatus for measurement of an enzymatic activity based on the present embodiments, the enzymatic activity measurement can be achieved through simple operations, and the activity of an enzyme present inside an in vivo tissue or an in vivo cell can also be measured.

Additional features and advantages are described herein, and will be apparent from the following Detailed Description and the figures.

DETAILED DESCRIPTION

Figure 1:
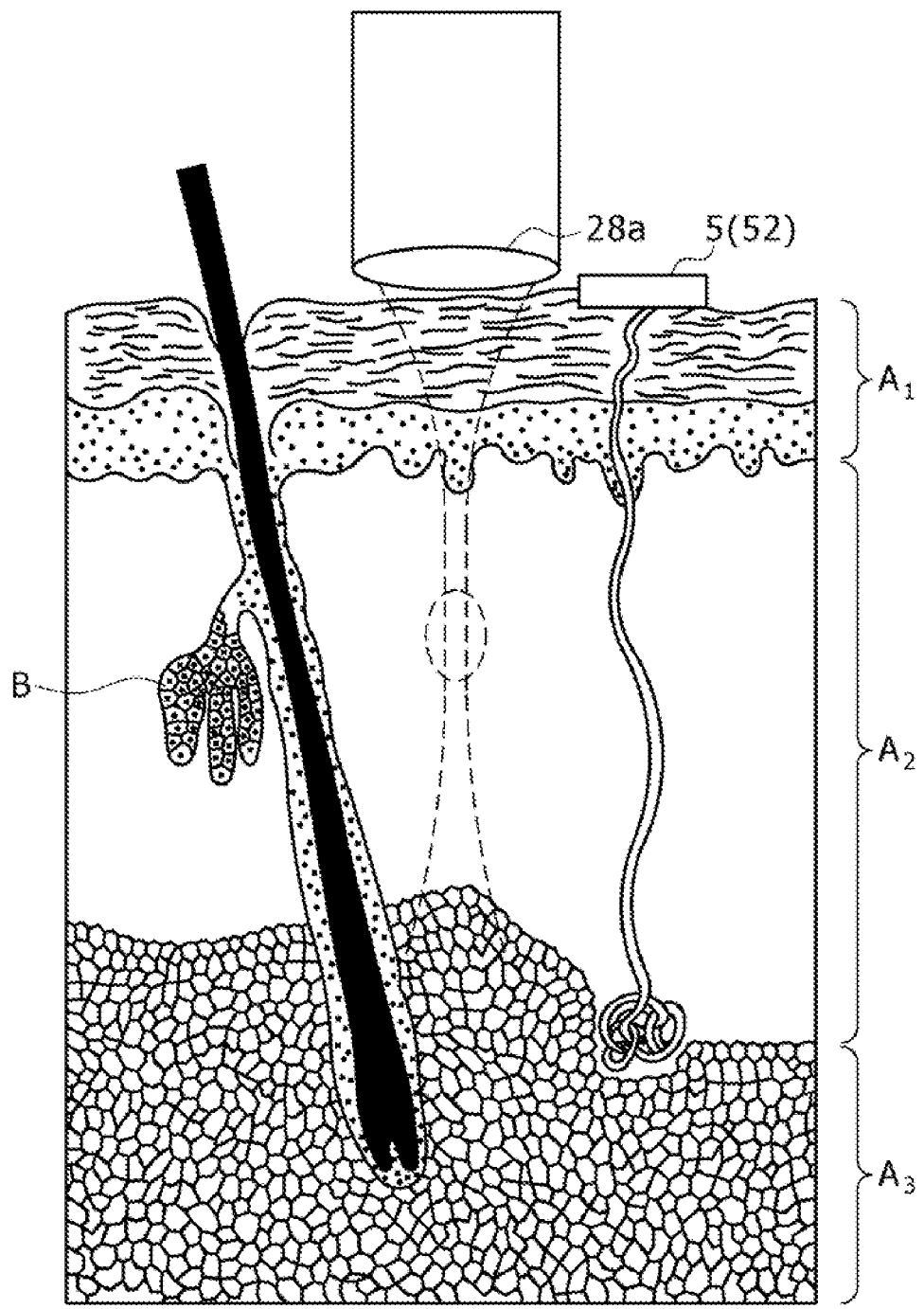
FIG. 1 is a schematic illustration of a method of measuring an enzymatic activity inside a skin tissue.

Now, embodiments will be described below with reference to the drawings. Incidentally, the following are merely representative examples, and the scope of the embodiments is not to be construed as limited to the examples.

In the method of measuring an enzymatic activity based on an embodiment, a substrate for an enzyme or a substrate metabolite produced on metabolism of the substrate by the enzyme is excited by multiple photon absorption, and a radiant wave resulting from the multiple photon excitation process of the substrate or substrate metabolite is detected. By the detection, the quantity of the substrate metabolite produced through the substrate metabolism by the enzyme is measured, and the enzymatic activity is evaluated thereby.

The measurement is carried out under such a condition that only one of the substrate and the substrate metabolite comes to generate the radiant wave through the multiple photon excitation process.

More specifically, for example, where the measurement is conducted under such a condition that only the substrate metabolite comes to generate the radiant wave through the multiple photon excitation process, the quantity of the substrate metabolite produced from the substrate by the activity of the enzyme, which is the object of measurement, is measured by detecting the radiant wave arising from the multiple photon excitation process of the substrate metabolite. In this case, as the intensity of the radiant wave after the lapse of a predetermined time is higher, the quantity of the substrate metabolite produced through the enzymatically induced metabolism is larger and, hence, the enzymatic activity is higher.

Here, the enzymatic activity (K) can be represented by the following formula (1):

$$K=|a(F_t-F_0)/(T-T_0)| \qquad (1)$$

where a is a correction factor, $T_0$ is measurement start time, T is a predetermined time after the start of measurement, $F_0$ is the value of radiant wave measured at time $T_0$, and $F_t$ is the value of radiant wave measured at time T.

Similarly, where the measurement is conducted under such a condition that only the substrate comes to generate the radiant wave through the multiple photon excitation process, the quantity of the substrate metabolite produced from the substrate by the activity of the enzyme, which is the object of measurement, is calculated from the reduction in the radiant wave arising from the multiple photon excitation process of the substrate. In this case, as the intensity of the radiant wave after the lapse of a predetermined time is lower, the quantity of the substrate metabolized by the enzyme is larger and, hence, the quantity of the substrate metabolize produced is larger, i.e., the enzymatic activity is higher.

As the substrate, a substrate specific to an enzyme or an enzyme group serving as the object of measurement is used. This makes it possible to measure only the activity of the enzyme serving as the object of measurement, distinctly from the activities of the many other enzymes. When a substrate common to an enzyme group composed of a plurality of enzymes (the substrate being not a substrate for other enzymes than those of the enzyme group) is used, the enzymatic activity of the enzyme group as a whole can be measured.

The substrate is selected, as required, according to the function of the enzyme serving as the object of measurement, and is selected from among chemical substances, lipids, amino acids, peptides, proteins, nucleic acids, etc. Examples of the label substrates (substrate reagents) in general use at present include DFH: (3-hydroxy-5,5-dimethyl-4-(4-methylsulfonylphenyl)-(5H)-furan-2-one), DFB: (3,4-difluorobenzyloxy)-5,5-dimethyl-4-(4-methylsulfonylphenyl)-(5H)-furan-2-one), and DFP: 3-(Isopropoxy)-5,5-dimethyl-4-(4-methylsulfonylphenyl)-5H-furan-2-one. These label reagents can be used also in the present embodiments.

The method of measuring an enzymatic activity according to an embodiment will now be described more in detail, taking the cytochrome P450 (hereinafter referred to as "CYP450"), which is a representative drug-metabolizing enzyme, as an object enzyme to be measured.

CYP450 is a gene superfamily composed of gene families including a plurality of molecular species. Each of the families, when being CYP1 family, for example, includes molecular species CYP1A1, CYP1A2, and CYP1B1. In relation to the human being, a total of about 50 kinds of molecular species have been reported. The molecular species have different substrate specificities, respectively. For example, it is known that CYP1A2 catalyze the N-deethylation of caffeine, and CYP1B1 catalyze the 4th-position hydroxylation of 17-β-estradiol.

The substrates for CYP450 include phenobarbital and many other drugs. For example, the drugs capable of serving as substrates for CYP1A2 include antidepressants such as amitriptyline hydrochloride, imipramine hydrochloride, clomipramine hydrochloride, mianserin hydrochloride, antiarrhythmic agents such as mexiletine hydrochloride, propranolol hydrochloride, propafenone hydrochloride, etc.

In this manner, the molecular species of CYP450 have respective specific substrates. Therefore, by designing and selecting the substrate according to the substrate specificity relevant to a given molecular species serving as the object of enzymatic activity measurement, the activity of the molecular species can be measures specifically. In the case of CYP2C9, for example, MFC: (7-Methoxy-trifluoromethylcoumarin) may be used as a substrate. Here, MFC per se does not fluoresce, but it comes to fluoresce when metabolized by CYP2C9 to be HFC: (7-Hydroxytrifluoromethylcoumarin).

In addition, when a specific substrate common to a plurality of molecular species is used, the enzymatic activity of a group of molecular species (a group of enzymes) can be measured.

In order to induce the multiple photon excitation process of a substrate or substrate metabolite, a femtosecond laser beam with a pulse width in the range from femtosecond order to picosecond order (sub-picosecond range) is used. As the laser beam, a mode-locked laser beam is used so as to realize the just-mentioned pulse width. For the mode-locked laser, titanium sapphire or erbium-added fiber laser medium or the like is adopted.

The near infrared femtosecond laser beam (hereinafter referred also to simply as "laser beam") has a wavelength of 650 to 1100 nm, and the wavelength is appropriately selected within this range according to the absorption wavelengths of the substrate and the substrate metabolite served to the measurement. To be more specific, in the case of a wavelength of 830 nm, for example, the pulse width is not more than 200 fs, and the repetition frequency is 80 MHz. Besides, the output stability is about ±0.5, and the mean beam output is about 2 W.

The near infrared femtosecond laser beam is condensed onto the focus where the enzyme as the object of measurement, the substrate and the substrate metabolite are present, by use of a condenser lens (objective lens). As the condenser lens, a lens transparent to infrared rays is used. The magnifying power of the lens is not particularly limited, and may appropriately be about 20 to 40 (times).

The substrate or substrate metabolite, in the vicinity of the focus (the site where the enzyme is present), simultaneously absorbs a plurality of photons from the condensed laser beam, thereby reaching the multiple photon excitation process. The substrate or substrate metabolite thus having made transition to an excited state generates a radiant wave when returning to its original energy state. By detecting the radiant wave, the quantity of the substrate metabolite produced upon the metabolism of the substrate by the enzyme can be measured.

The detection of the radiant wave is conducted by a method in which the radiant wave arising from the multiple photon excitation process of the substrate or substrate metabolite is condensed by the condenser lens and guided to a photoelectric conversion element. The photoelectric conversion element detects the radiant wave, converts the intensity of the wave into electrical data, and outputs the data to a computer in connection therewith.

The enzyme to be the object of measurement can include any of various enzymes. Under in vitro conditions, an enzymatically active fraction prepared from a tissue homogenate or cell lysate by a method according to the related art can be used. In addition, an enzyme which has been isolated and purified, and a protein of which the function is unknown and which is to be checked for the presence or absence of a specified enzymatic activity therein, can also be used. Such an object of measurement is added to a substrate-containing buffer to effect an enzyme reaction, and the substrate or substrate metabolite in the buffer is subjected to multiple photon excitation, to thereby measure the enzymatic activity. Incidentally, the method of measuring an enzymatic activity according to an embodiment is applicable not only to measurement under in vitro conditions but also to measurement of an enzyme present inside an in vivo tissue or an in vivo cell (measurement under in vivo conditions). The measurement of enzymatic activity under in vivo conditions will be detailed later.

In carrying out the measurement, not only the enzyme and the substrate but also an enzymatic activity promoter or inhibitor may be added to the buffer, whereby the enzymatic activity promoting or inhibiting activity of the enzymatic activity promoter or inhibitor can be evaluated.

Besides, not only the enzyme and the substrate but also a candidate compound (specimen) for an enzymatic activity promoter or inhibitor may be added to the buffer, whereby it can be evaluated whether or not the specimen has the enzymatic activity promoting or inhibiting activity. This permits screening of activity promoters or inhibitors with respect to a specified enzyme.

In this case, the enzymatic activity promoting or inhibiting activity (S) can be represented by the following formula (2):

$$S=|(b(F_t b-F_0)/(T-T_0))/(a(F_t-F_0)/(T-T_0)|  \quad (2)$$

where a and b are correction factors, $T_0$ is the measurement start time, T is a predetermined time after the start of measurement, $F_0$ is the value of the radiant wave measured at time $T_0$, $F_t$ is the value of the radiant wave measured at time T in the absence of the enzymatic activity promoter or inhibitor, and $F_t b$ is the value of the radiant wave measured at time T in the presence of the enzymatic activity promoter or inhibitor.

Now, the measurement of enzymatic activity under in vivo conditions will be described below. The near infrared femtosecond laser beam is characterized by a longer wavelength and a lower energy, as compared to the laser beams used for single photon excitation according to the related art. In addition, since excitation is effected by a plurality of photons in the case of the near infrared femtosecond laser beam, only the molecules in the vicinity of the focus can be excited. Therefore, the multiple photon excitation by the near infrared femtosecond laser beam provides a high depth reaching performance. Also, it is advantageous in that the measurement can be conducted for a long time while restraining fluorescence photobleaching or damage from occurring at other positions in the sample than the focus.

In view of these advantages, the method of measuring an enzymatic activity by utilizing the multiple photon excitation process can be said to be an optimum method for measuring an enzymatic activity inside an in vivo tissue or an in vivo cell. The characteristic feature that a high depth reaching performance can be obtained means that it is possible to measure the activity of an in vivo enzyme present in the inside (the depth) of an in vivo tissue. Besides, the feature that it is possible to restrain fluorescence bleaching or damage from occurring at other positions in the sample than the focus makes it possible to conduct real-time measurement for a long time, without injuring the tissue or cells (namely, in a noninvasive manner). Therefore, according to the method of measuring an enzymatic activity through utilization of the multiple photon excitation process, the activity of an enzyme present inside an in vivo tissue or an in vivo cell can be directly measured, without need to prepare a tissue homogenate or cell lysate, which has been necessary in the methods according to the related art.

Now, a specific method for carrying out the method of measuring an enzymatic activity based on an embodiment will be described below, taking a skin as an example of the in vivo tissue. FIG. 1 is a schematic illustration of a method of measuring an enzymatic activity in a skin tissue.

In FIG. 1, symbol $A_1$ denotes an epidermis, $A_2$ a dermis, and $A_3$ a subcutaneous tissue. The skin constituting the measurement site is desirably a skin site where the surface is flat and smooth, hair is absent, and the epidermis is thin. For example, a skin site in the range from the back of the elbow to the wrist, of a forearm, is preferable. Selection of such a site ensures that the laser beam can be prevented from absorption or scattering at the living body surface, and the radiant wave can be detected efficiently. Further, when water, an oil or the like is applied to the skin surface so as to prevent the laser beam from being scattered on the living body surface, the measurement accuracy can be further enhanced.

The near infrared femtosecond laser beam (indicated by broken line, in the figure) is condensed by a condenser lens 28a onto one point (focus) which is located in the dermis $A_2$ and which is the site where the object enzyme for measurement is present, in the figure. In this case, the near infrared femtosecond laser beam undergoes little absorption into water or blood in the skin tissue and little scattering by the tissue, and exhibits a high depth reaching performance.

During the measurement, the measurement site is shielded so as to preclude penetration of environmental light. The laser beam for irradiation therewith causes excitation particularly in a fusiform region (the elliptic region surrounded by the dotted line, in the figure) with a diameter of about 500 μm in XY plane and a size of about 1 mm in Z-axis direction. The excitation occurs at a depth (from the skin surface) of 5 mm, corresponding to the operating distance of the condenser lens 28a.

The measurement site is coated with a substrate specific to the enzyme serving as the object of activity measurement. The substrate thus applied permeates into the skin tissues and into tissue cells, to be introduced to the site where the enzyme is present. For example, in the case of measuring the enzymatic activity of the above-mentioned CYP2C9, MFC (7-Methoxy-trifluoromethylcoumarin) is dissolved in DMSO (dimethyl sulfoxide) in a concentration of about 2.5 μM, and the solution is applied to the epidermis. Besides, a method may be adopted in which the substrate is caused to penetrate to the measurement site sustainably or intermittently from a penetration device denoted by symbol 5 in FIG. 1. The penetration device 5 includes not only a penetrating part 52 shown in the figure but also a liquid feed line for supplying the penetrating part 52 with a substrate solution, a main body, etc. The penetration device 5 will be detailed later.

While the case where CYP2C9 is used as the object enzyme for measurement and MFC is used as the substrate will be described below, the enzyme and the substrate are not limited to these ones. Any combination of an enzyme and a substrate specific to the enzyme may be used.

Upon permeating to the skin site where CYP2C9 is present, MFC reacts with CYP2C9, to be thereby metabolized into HFC (7-Hydroxytrifluoromethylcoumarin). The quantity of HFC is measured by detecting the radiant wave (in this case, fluorescence) arising from the multiple photon excitation process of HFC. In the above-mentioned formula (1), $T_0$ is the time immediately before application of MFC to the measurement site (the measurement start time), T is a lapse of time after the MFC application, $F_0$ is the value of fluorescence measured at time $T_0$ (the value of fluorescence in the condition where nothing has been applied to the measurement site), and $F_t$ is the value of fluorescence measured at time T.

With the time of application of MFC to the measurement site as a reference, real-time measurement of fluorescence intensity is conducted at intervals of 5 minutes, for example. For the detection of fluorescence from HFC, an optical filter with a center wavelength of 520 nm and a wavelength range of 50 nm is used.

This makes it possible to perform real-time measurement of the enzymatic activity of CYP2C9 present in the dermis $A_2$. In this case, invasiveness to the skin is extremely slight, so that the real-time measurement can be performed for a long time while little injuring the skin.

Further, where it is desired to inspect the enzymatic activity promoting or inhibiting activity of an enzymatic activity promoter or inhibitor for CYP2C9, the enzymatic activity promoter or inhibitor is applied to the measurement site, in the same manner as MFC. Besides, the enzymatic activity promoter or inhibitor may be caused to permeate into the measurement site, by use of the penetration device 5.

MFC and the enzymatic activity promoter or inhibitor may be caused to permeate either mixedly or separately. In the case of causing MFC and the enzymatic activity promoter or inhibitor to separately permeate by use of the penetration device 5, two penetration devices 5 are needed, one for MFC and one for the promoter or inhibitor; thus, the two penetration devices 5 are disposed on the epidermis $A_1$ in the vicinity of the measurement site.

As for the sequence of applying the substrate and the enzymatic activity promoter or inhibitor to the measurement site, it is preferable to apply the enzymatic activity promoter or inhibitor prior to the substrate first. In this case, the time immediately before application of the substrate is assumed to be $T_0$ (the measurement start time) (refer to the above-mentioned formula (2)).

$F_t$ (the value of the radiant wave measured at time T in the absence of the enzymatic activity promoter or inhibitor) and $F_tb$ (the value of the radiant wave measured at time T in the presence of the enzymatic activity promoter or inhibitor) are measured repeatedly, at varied measurement sites. For example, in the case of the forearm portion ranging from the back of the elbow to the wrist, it is desirable to repeat the measurement under measurement conditions as even as possible, for example, to repeat the measurement at positions spaced by several centimeters from each other.

Also, in the case of screening enzymatic activity promoters or inhibitors for CYP2C9, each of candidate compounds (specimens) is applied to the measurement site or caused to permeate into the measurement site by use of the penetration device 5, in the same manner as above. Besides, MFC and the specimen may be caused to penetrate either mixedly or separately, in the same manner as above.

The case where the object enzyme for measurement is CYP2C9 has now been particularly described, taking the skin as an example of the in vivo tissue. While the description has been made of the case where the skin portion to be the object of measurement is the dermis $A_2$, it is also possible, for example, to measure the enzymatic activity in a sebaceous gland tissue denoted by symbol B in the figure. Further, examples of the in vivo tissues capable of constituting the object of measurement in the embodiment include not only the skin but also nails, ears, fingertips, lips of mouth, retina, thrix, and so on. Besides, the in vivo tissues applicable are not limited to these tissues exposed to the body surface, but include viscera such as liver, brain, kidney, muscles, etc. In order to measure the enzymatic activity in a viscus tissue, the laser beam is guided to a measurement site in the viscus by use of an optical fiber, and the radiant wave is condensed. The measurement by use of an optical fiber is considered to be applicable to measurement of an enzymatic activity in the tissue of a diseased portion (operated portion), at the time of endoscopy or celiotomy or the like.

Figure 2:
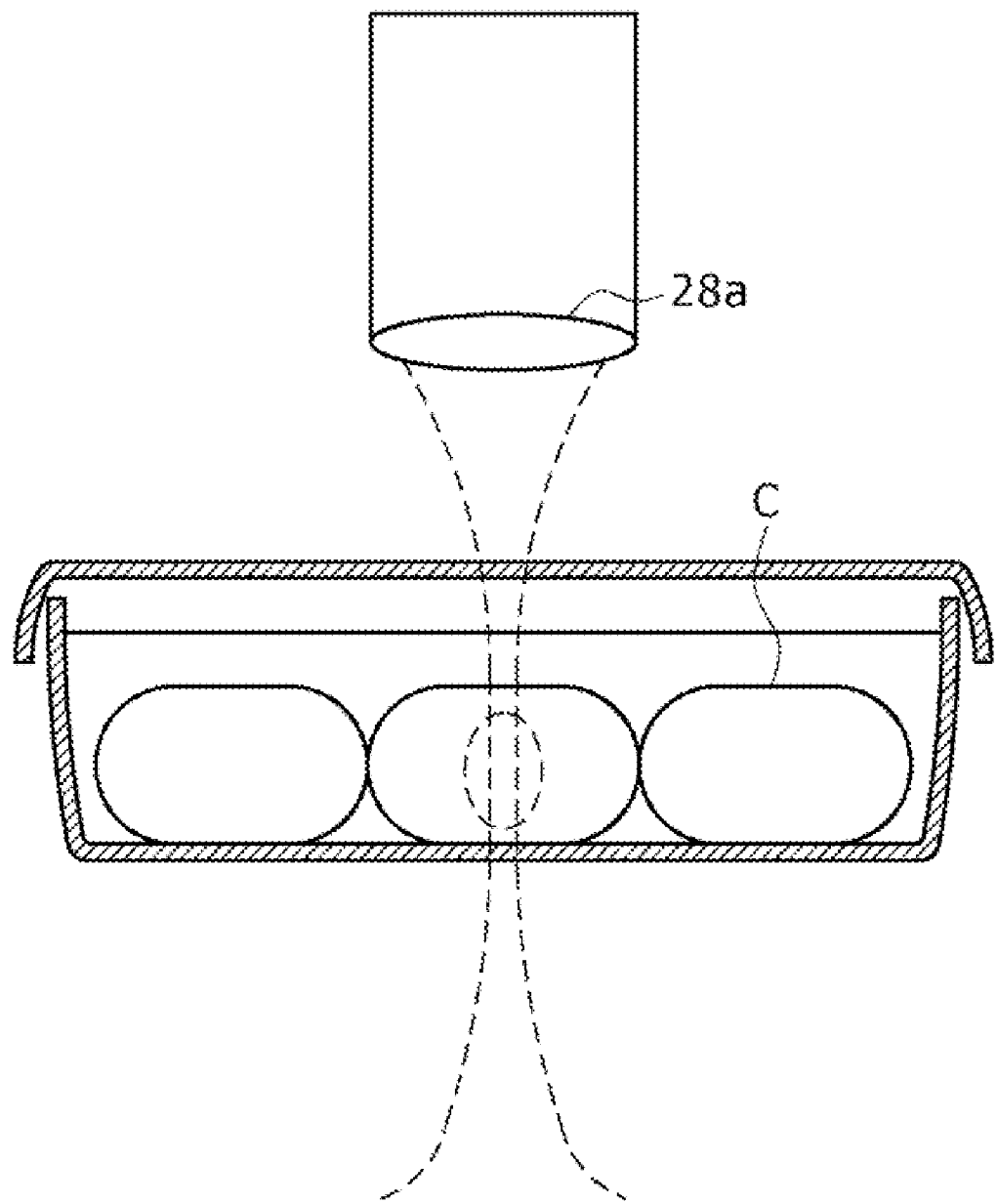
FIG. 2 is a schematic illustration of a method of measuring an enzymatic activity inside an in vivo cell.

FIG. 2 is a schematic illustration of a method of measuring an enzymatic activity inside an in vivo cell.

In FIG. 2, symbol C denotes a cultured cell. In the figure, the cultured cells C are shown in the state of being cultured in a Petri dish. The vessel for the culture of cells is not particularly limited; not only the Petri dish but also flask, chamber slide and the like may be used, provided the material of the vessel is transparent to the laser beam.

A near infrared femtosecond laser beam (indicated by broken lines, in the figure) is condensed by a condenser lens 28a into a cultured cell C, which is the site where the object enzyme for measurement is present, in the figure. In this case, by condensing the laser beam into a specified intracellular organelle such as nucleus, mitochondria, Golgi body, etc., it is possible to measure the activity of an enzyme present in such an intracellular organelle. During the measurement, light shielding is made so as to prevent penetration of environmental light.

In conducting the measurement, a substrate specific to the enzyme serving as the object of measurement is added to the culture solution. The substrate thus added permeates into the cultured cell, and it introduced to the site where the enzyme is present. For example, in the case of measuring the enzymatic activity of the above-mentioned CYP2C9, MFC (7-Methoxy-trifluoromethylcoumain) is dissolved in DMSO (dimethyl sulfoxide) in a concentration of about 5 µm, and the solution is added to the cultured cell. Besides, in the case of using a substrate which is low in cytoplasmic membrane permeability, the substrate can be introduced into the cultured cell by use of such a technique as micro-injection.

When it is desired to inspect the enzymatic activity promoting or inhibiting activity of an enzymatic activity promoter or inhibitor for CYP2C9, the promoter or inhibitor is added to the culture solution, in the same manner as MFC. In this case, MFC and the enzymatic activity promoter or inhibitor may be added either mixedly or separately.

Also, in the case of screening enzymatic activity promoters or inhibitors for CYP2C9, a candidate compound (specimen) is added to the culture solution. In this instance, MFC and the specimen may be added either mixedly or separately, in the same manner as above.

Figure 3:
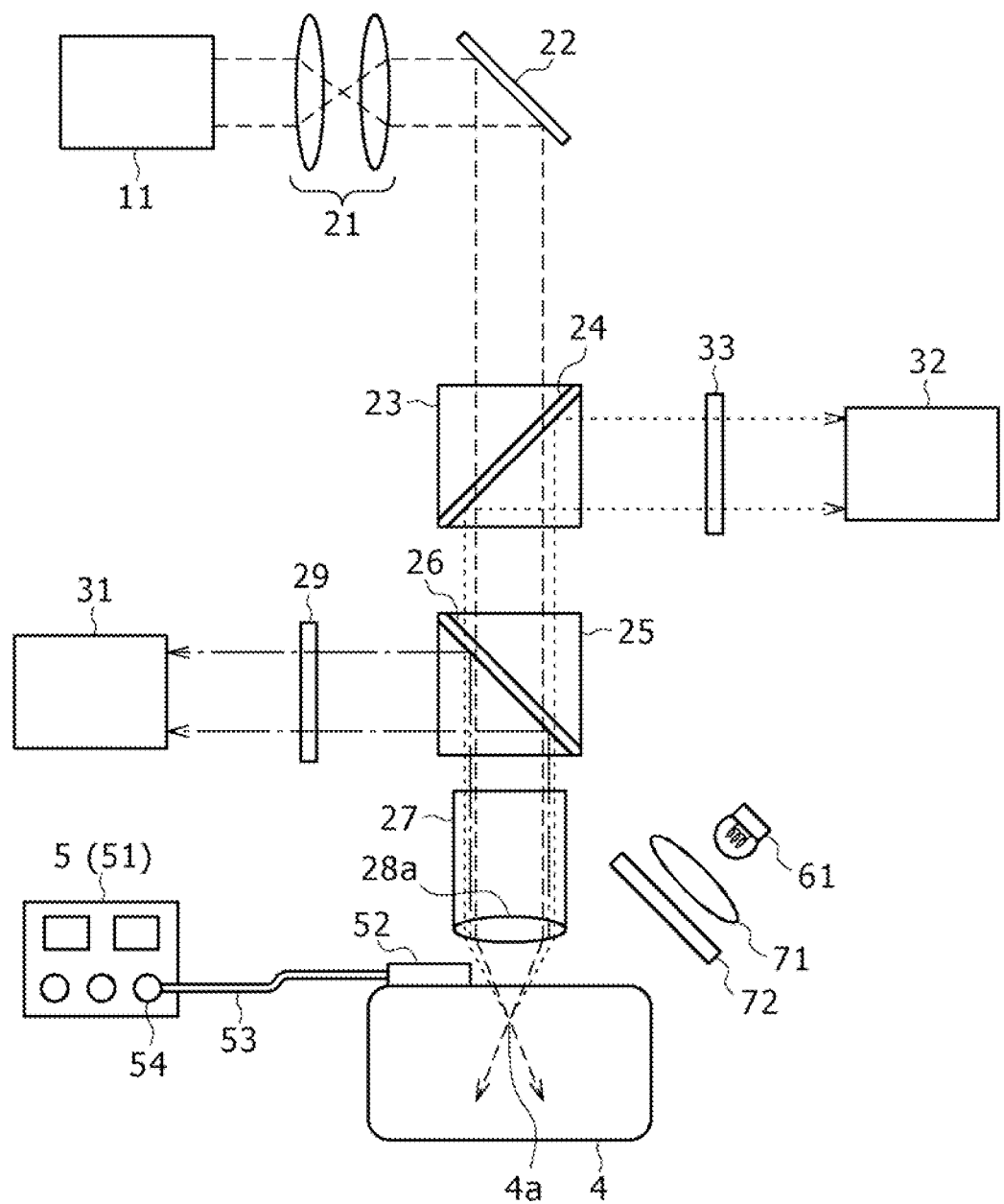
FIG. 3 is a block diagram of a first embodiment of the apparatus for measuring an enzymatic activity.

Now, the apparatus for measuring an enzymatic activity according to an embodiment will be described below. FIG. 3 is a block diagram showing a first embodiment. The basic structure of the apparatus for measuring an enzymatic activity according to an embodiment can be obtained by diverting the system of a known near infrared multiple photon excitation upright microscope. Now, the structure will be briefly described below, based on the drawing.

In FIG. 3, symbol 11 denotes a laser beam source capable of oscillating with near infrared pulses. The laser beam (indicated by broken lines, in the figure) emitted from the laser beam source 11 is transmitted through a laser beam diameter controller 21 for controlling the laser beam diameter, and is reflected by a Galvano mirror 22 functioning for laser beam scanning on a sample 4.

Subsequently, the laser beam enters a beam splitter 23, which includes an optical system using a dichroic filter, a dichroic mirror, or the like. A band-pass filter 24 used in this embodiment transmits the laser beam therethrough, and, at the same time, reflects a reflected wave (indicated by dotted lines, in the figure) coming from the sample 4 being irradiated with light of a wavelength of 600 to 950 nm from a light source 61, while absorbing or attenuating a specified wavelength, toward a CCD camera unit 32 described later.

The laser beam transmitted through the band-pass filter 24 is guided to a beam splitter 25. Like the beam splitter 23, the beam splitter 25 includes an optical system using a dichroic filter, a dichroic mirror, or the like. The dichroic mirror 26 used in this embodiment transmits the laser beam from the laser beam source 11 therethrough. In addition, the dichroic mirror 26 selects a specified wavelength from the radiant wave coming from the sample 4, reflects the selected wavelength wave to a radiant wave detection unit 31 described later, and, simultaneously, transmits the reflected wave toward the beam splitter 23.

The laser beam transmitted through the dichroic mirror 26 is condensed by a condenser lens 28a attached to a focal point control mechanism 27, onto a focal point 4a in the sample 4. The condenser lens 28a, the laser beam diameter controller 21, the band-pass filter 24, and the dichroic mirror 26 used here are transparent to infrared rays. This applies also to other optical filters, unless otherwise specified. Besides, the magnifying power of the condenser lens 28a is not particularly limited, and is appropriately about 20 to 40 (times).

The laser beam thus condensed induces a multiple photon excitation process of the substrate and the substrate metabolite at the focal point 4a. The condenser lens 28a is mounted in the focal point control mechanism 27 so that its position in the vertical (height) direction in the figure can be controlled. This ensures that the position in the vertical (depth) direction of the focal point 4a in the sample 4 can be controlled.

In addition, the condenser lens 28a functions also to condense the radiant wave generated from the focal point 4a and the reflected wave (both waves are indicated respectively by dot-dash lines and dotted lines, in the figure) for guiding the waves to the radiant wave detection unit 31 and the CCD camera unit 32, respectively. Of the condensed radiant wave, first, a specified wavelength is reflected by the dichroic mirror 26. The reflected radiant wave is further transmitted through a short-pass filter 29, to be guided to the radiant wave detection unit 31. Incidentally, the short-pass filter 29 has such a characteristic as to intercept wave components of not less than a specified wavelength.

The radiant wave detection unit 31 has the function of selectively receiving a specified wavelength, and at least one such radiant wave detection unit 31 is used. The radiant wave detection unit 31 includes a photoelectric conversion element for detecting the radiant wave. To the radiant wave detection unit 31, a computer (not shown) for storing and processing data sent from the photoelectric conversion element is connected. The photoelectric conversion element detects the radiant wave, converts the intensity of the radiant wave to electrical data, and outputs the data to the computer connected therewith. From the data (the measured value of the radiant wave), the enzymatic activity (K) is calculated by use of the above-mentioned formula (1).

As has been described above, the apparatus for measuring an enzymatic activity according to an embodiment includes the laser beam source 11, the radiant wave detection unit 31, and the optical path through which the laser beam is introduced into the site where the enzyme is present in the sample 4 and through which the radiant wave is introduced into the radiant wave detection unit 31. Here, the "optical path" includes at least the Galvano mirror 22, the beam splitter 25, and the condenser lens 28a.

In addition, as shown in FIG. 3, the optical path may include the beam splitter 23 for guiding the reflected wave from the sample 4 to the CCD camera unit 32 for detecting the reflected wave. The reflected wave (indicated by dotted lines, in the figure) condensed by the condenser lens 28a and transmitted through the dichroic mirror 26 of the beam splitter 25 is reflected by the band-pass filter 24 of the beam splitter 23, to be guided to the CCD camera unit 32. Incidentally, a long-pass filter 33 is provided at a stage precedent to the CCD camera unit 32. The long-pass filter 33 has such a characteristic as to intercept wave components of not more than a specified wavelength.

An image display device (not shown) is connected to the CCD camera unit 32. This ensures that, by using an ordinary white light source 61 serving for illumination by an epi-illumination system, the site of irradiation with the laser beam can be determined while checking the sample on a monitor through the CCD camera unit 32 (which has sensitivity also in the infrared region) and the image display device. Since the CCD camera unit 32 has sensitivity also in the infrared region, in the case where the sample 4 is a skin, for example, a subcutaneous portion (the inside of the sample 4) can also be observed by utilizing the permeability of infrared rays through the skin. The epi-illumination system includes the light source denoted by symbol 61 in the figure, a beam diameter controller denoted by symbol 71, and a long-pass filter denoted by symbol 72. Incidentally, the epi-illumination light coming from the light source 61 down to the sample 4 is omitted in the figure.

The near infrared femtosecond laser beam used as the laser beam source has a wavelength of 650 to 1100 nm, and the wavelength is appropriately selected in the range according to the absorption wavelengths of the substrate and the substrate metabolite served to the measurement. More specifically, in the case of a wavelength of 830 nm, for example, the pulse width is not more than 200 fs, and the repetition frequency is 80 MHz. Besides, the output stability is about ±0.5, and the mean beam output is about 2 W.

In this case, the radiant wave detected by the radiant wave detection unit 31 has a wavelength of 500 to 600 nm (fluorescence), for example, whereas the wavelength of the reflected wave detected by the CCD camera unit 32 is 600 to 950 nm.

The wavelength of the laser beam and the wavelength of the radiant wave detected at the radiant wave detection unit 31 vary depending on the wavelength of the radiant wave arising from the multiple photon excitation process of the substrate and the substrate metabolite served to the measurement. The characteristics of the band-pass filter 24, the dichroic mirror 26, and the short-pass filter 29 to be used are optimally selected according to the substrate and the substrate metabolite relevant to the measurement.

Examples of the sample 4 include a variety of tissues exposed to the body surface, such as the skin, nails, ears, fingertips, lips of mouth, retina, and thrix (see FIG. 1, also). Besides, where the sample 4 is a cultured cell, the enzymatic activity inside an in vivo cell can also be measured, as shown in FIG. 2.

In addition, particularly where the sample 4 is an in vivo tissue such as a skin, a configuration may be adopted in which the apparatus for measuring an enzymatic activity is provided with the penetration device 5 in addition to the above-mentioned components and in which a substrate, an enzymatic activity promoter or inhibitor, and a specimen are caused to permeate into the measurement site where the enzyme is present.

The penetration device 5 includes the main body 51, the penetrating part 52, and the liquid feed line 53. The main body 51 has a reservoir for reserving a substrate solution, and the substrate solution is supplied through the liquid feed line 53 to the penetrating part 52. The penetrating part 52 is disposed in the vicinity of the measurement site, and causes the substrate solution supplied from the main body 53 to permeate to the site where the enzyme is present. In addition, the penetration device 5 is used also in the case where a solution of an enzymatic activity promoter or the like is made to permeate. In this case, a plurality of penetrating parts 52 and a plurality of liquid feed lines 53 are connected to the main body 51, and function for supplying the enzymatic activity promoter or inhibitor solution and the like, respectively.

The main body 51 is provided with valves 54 for controlling the quantities of the substrate solution and the like supplied to the penetrating parts 52. The liquid feed lines 53 are connected to the main body 51 through the valves 54. The valves 54 permit the substrate solution and the like to be supplied sustainedly or intermittently in quantities controlled respectively.

As the main body 51, a device having an ordinary pump function can be use. In addition, the main body 51 is desirably provided with a mechanism by which the quantity of the substrate solution or the like can be controlled, such as the valve 54. Besides, the penetrating part 52 is brought into contact with the in vivo tissue such as skin in the state of being wetted with the substrate solution or the like, and therefore desirably has such a configuration that the solution is not evaporated. Specifically, a microanalyzer is preferably used.

Figure 4:
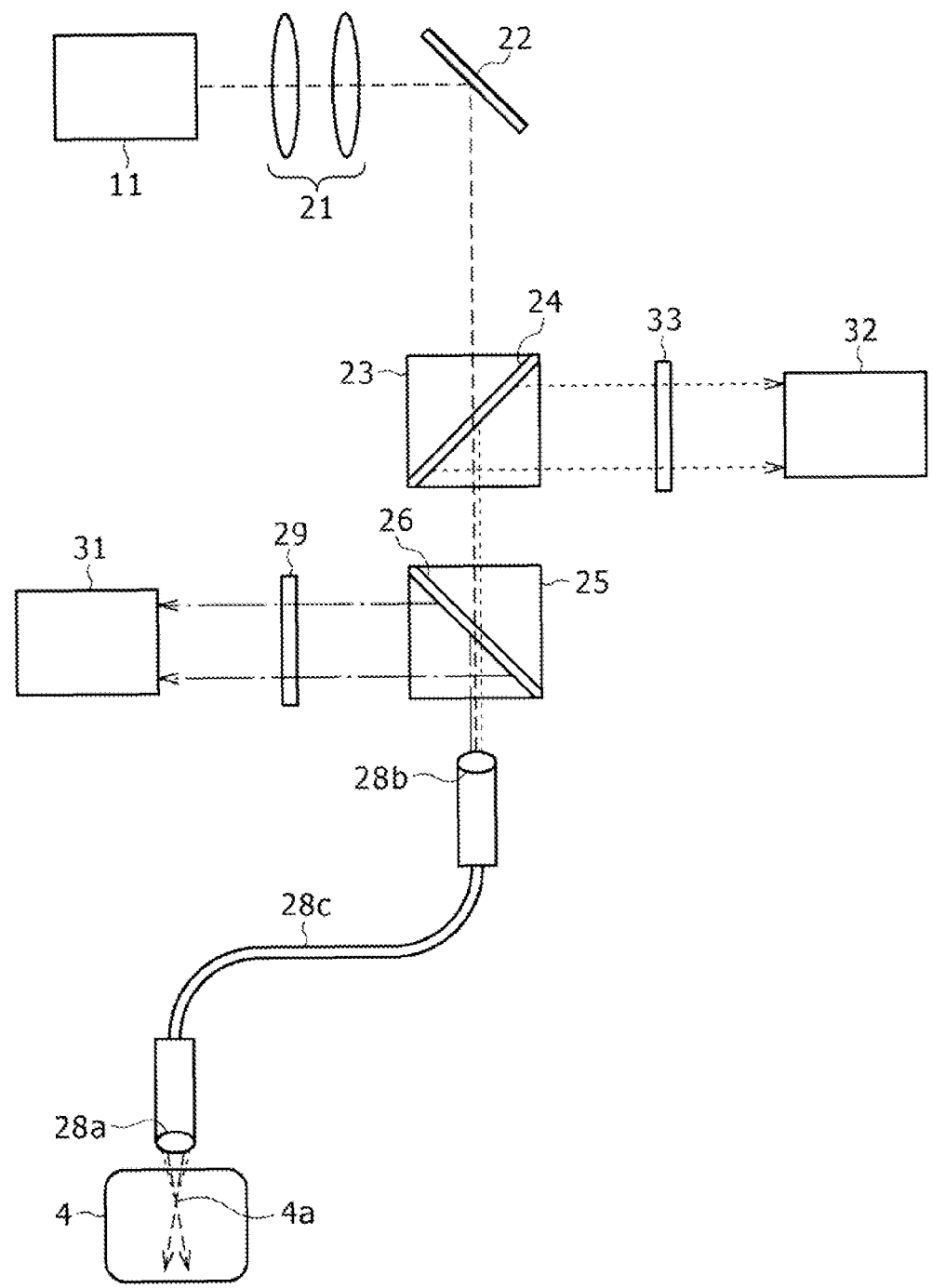
FIG. 4 is a block diagram of a second embodiment of the apparatus for measuring an enzymatic activity.

FIG. 4 is a block diagram showing a second embodiment of the apparatus for measuring an enzymatic activity. In this figure, the laser beam, the radiant wave and the reflected wave are partly simplified.

The apparatus for measuring an enzymatic activity shown in FIG. 4 has an optical fiber 28c for transmitting the laser beam, the radiant wave and the reflected wave. The apparatus for measuring an enzymatic activity is for application to the case where the sample 4 is a viscus such as liver, brain, kidney, muscle, etc. The apparatus is so designed that the laser beam can be transmitted through the optical fiber 28c, to be radiated to such a viscus.

The laser beam emitted from a laser beam source 11 is transmitted through a dichroic mirror 26 of a beam splitter 25, is then guided by a condenser lens 28b into the optical fiber 28c, and is transmitted through the optical fiber 28c to a condenser lens (objective lens) 28a. Subsequently, the laser beam is condensed by the condenser lens 28a onto a focal point 4a in the sample 4, to induce multiple photon excitation process of the substrate and the substrate metabolite.

The radiant wave generated from the focal point 4a due to the multiple photon excitation process of the substrate and the substrate metabolite (as well as the reflected wave) is condensed by the condenser lens 28a, and is transmitted through the optical fiber 28c, to be guided to the radiant wave detection unit 31 and the CCD camera unit 32.

The measurement of an enzymatic activity in a viscus tissue is expected to be carried out at the time of endoscopy or celiotomy or the like. Therefore, it is desirable that the condenser lens 28a and the optical fiber 28c are as small as possible.

Finally, description will be made of the enzyme as the object of measurement in the embodiment. The object enzyme for measurement is not particularly limited, and may include any of various enzymes under in vitro conditions and under in vivo conditions, as has been described above. Enzymatically active fractions which are prepared from tissue homogenates or cell lysates, enzymes which are isolated and purified, proteins of which the functions are unknown and which are to be checked for the presence or absence of an enzymatic activity therein, and the like can also be the objects of measurement here.

Especially preferable examples of the object of measurement include drug-metabolizing enzymes. The drug-metabolizing enzymes are groups of enzymes capable of metabolizing various chemical substances in vivo, such as CPY450, N-acetyltransferase (NAT-2), methyltransferase (TPMT), etc.

It has been known that the drug responses such as drug efficacy and side effects involve individual differences and racial differences. Therefore, depending on the patient, an unexpected side effect may appear, or it may be impossible to obtain the expected drug efficacy, due to insufficient dose. Taking this into account, in recent years, there have been made attempts to realize the so-called tailor-made medicine in which an appropriate drug is selected according to the condition of the disease and the constitution of the patient, so as to produce the best therapeutic effect.

One of the major causes of the individual differences in drug response is the genetic polymorphism of drug-metabolizing enzymes. The genetic polymorphism observed with respect to a drug-metabolizing enzyme directly affects the activity of the enzyme relating to the metabolism of a drug and the kinetics thereof, and has an intimate relationship with the drug response of the individual.

At present, a large-scale gene analysis by collecting a large number of cases is being conducted in regard of the relationship between the genetic polymorphism and the drug response. As to CYP450, which is a representative drug-metabolizing enzyme, a genetic polymorphism decision technology using the DNA microarray technique has already been put to practical use, and the relationships between the enzymatic activities and the genetic polymorphism are being elucidated.

According to the method and apparatus for measuring an enzymatic activity based on embodiments, the activity of a drug-metabolizing enzyme inside an in vivo tissue can be directly measured, without needing such a DNA-based analysis. Therefore, it is possible to grasp the characteristic features of the activities of the drug-metabolizing enzymes with respect to an individual patient, more easily and swiftly. For example, if a doctor can accurately evaluate the activity of CYP450 present in the tissue of a diseased portion at the time of diagnosis or a surgical operation, it is useful for finding the risk of side effects and determining the appropriate dose, at the time of subscribing a drug.

The method and apparatus for measuring an enzymatic activity according to embodiments can be utilized for measurement of an enzymatic activity inside an in vivo tissue or an in vivo cell, in the fields of, for example, pharmaceutical research and development, pharmacological tests, safety tests, etc. In addition, the method and apparatus can be utilized also for quality inspections for checking whether or not the activity of an enzyme has been expressed to a desired extent in, for example, in a gene-modified animal or cell line obtained by gene manipulation of a specified enzyme.

Furthermore, the method and apparatus for measuring an enzymatic activity based on embodiments permits a doctor to grasp the characteristics of the enzymatic activities in the individual patient, to evaluate the drug-metabolizing powers, etc. and to prescribe an appropriate drug or drugs, thereby contriving to realization of the so-called tailor-made medicine.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An in vivo method of measuring an enzymatic activity of a drug-metabolizing enzyme comprising:
   providing a drug specific to the drug-metabolizing enzyme to an in vivo measurement site that includes the drug-metabolizing enzyme;
   inducing a multiple photon excitation process of the drug or a drug metabolite that is produced upon metabolization of the drug by the drug-metabolizing enzyme; and
   determining enzymatic activity by measuring the quantity of the drug metabolite that is produced upon metabolization of the drug by the drug-metabolizing enzyme, through detecting a radiant wave generated from the multiple photon excitation process of said drug or said drug metabolite,
   wherein the multiple photo excitation process is induced by condensing a laser beam having a pulse width in the range of femtosecond order to picosecond order.

2. The method of measuring the enzymatic activity as set forth in claim 1, which is carried out under such a condition that only one of said drug and said drug metabolite generates said radiant wave through said multiple photon excitation process.

3. The method of measuring the enzymatic activity as set forth in claim 1, wherein said drug-metabolizing enzyme is an in vivo enzyme, and said drug is caused to penetrate into the in vivo measurement site where said drug-metabolizing enzyme is present.

4. The method of measuring the enzymatic activity as set forth in claim 1, wherein the radiant wave includes fluorescent light.

5. The method of measuring the enzymatic activity as set forth in claim 1, wherein inducing the multiple photon excitation process of the drug or the drug metabolite is performed by irradiating the in vivo measurement site with the laser beam.

6. The method of measuring the enzymatic activity as set forth in claim 1, wherein the laser beam is a near infrared laser beam having a wavelength of 650 nm to 1100 nm.

7. The method of measuring the enzymatic activity as set forth in claim 1, wherein the laser beam is condensed using an objective lens.

8. The method of measuring the enzymatic activity as set forth in claim 1, wherein the radiant wave is detected using a photoelectric conversion element.

9. The method of measuring the enzymatic activity as set forth in claim 1, wherein the drug is provided to the in vivo measurement site by coating the measurement site with the drug.

10. The method of measuring the enzymatic activity as set forth in claim 1, wherein the laser beam is transmitted through an optical fiber.

11. The method of measuring the enzymatic activity as set forth in claim 1, wherein the drug-metabolizing enzyme is selected from the group consisting of cytochrome P450 enzymes, N-acetyltransferase enzymes and methyltransferase enzymes.

* * * * *